US007243799B2

(12) United States Patent
Hague

(10) Patent No.: US 7,243,799 B2
(45) Date of Patent: Jul. 17, 2007

(54) PORTABLE CONTAINER FOR DISPOSING OF A MEDICATED ORAL DOSAGE FORM

(75) Inventor: Brian Hague, Bountiful, UT (US)

(73) Assignee: Cephalon, Inc., Frazer, PA (US)

( * ) Notice: Subject to any disclaimer, the term of this patent is extended or adjusted under 35 U.S.C. 154(b) by 337 days.

(21) Appl. No.: 10/145,587

(22) Filed: May 14, 2002

(65) Prior Publication Data

US 2002/0197196 A1 Dec. 26, 2002

Related U.S. Application Data

(60) Provisional application No. 60/291,032, filed on May 15, 2001.

(51) Int. Cl.

*B65D 83/04* (2006.01)
*B65D 85/00* (2006.01)
*B65D 50/00* (2006.01)
*B08B 3/08* (2006.01)
*A61L 2/16* (2006.01)

(52) U.S. Cl. ............................ 206/540; 134/93; 206/5; 215/201; 422/119; 422/270

(58) Field of Classification Search ................ 206/540, 206/0.5; 215/201, 385; 220/229, 676; 134/42, 134/93, 182, 198; 422/119, 265, 270; 68/17 R; 510/277

See application file for complete search history.

(56) References Cited

U.S. PATENT DOCUMENTS 1,580,104 A 4/1926 Hasselmann et al.
2,332,030 A * 10/1943 Toronto ...................... 422/270
2,436,291 A 2/1948 Daniel et al.
3,088,634 A * 5/1963 Rosekrans et al. ........... 206/0.5
3,607,103 A * 9/1971 Kiefer ........................ 206/0.5
3,792,979 A * 2/1974 Clinton ...................... 422/265
3,899,100 A 8/1975 Rigaud
3,907,145 A 9/1975 Horvath
4,116,329 A 9/1978 Garden
4,141,461 A 2/1979 LaChance
4,340,148 A 7/1982 Beckham
4,454,944 A 6/1984 Shillington et al.
4,502,606 A 3/1985 Shillington et al.
4,519,513 A 5/1985 Weiler et al.
4,600,112 A 7/1986 Shillington et al.
4,671,953 A 6/1987 Stanley et al.
4,789,639 A 12/1988 Fleming
4,803,998 A 2/1989 Kezes et al.
5,024,327 A 6/1991 Shillington
5,064,083 A 11/1991 Alexander et al.

(Continued)

*Primary Examiner*—Bryon P. Gehman

(57) ABSTRACT

The present invention includes a disposal system for disposal of medicated oral dosage forms comprising: 1) a container having a top, a bottom, and a sidewall, the container having a plurality of apertures located thereon; 2) a uni-directional port for securing a medicated oral dosage form within the container wherein the uni-directional port allows the medicated oral dosage form to be easily inserted into the container, but prevents the medicated oral dosage form from being removed from the container such that the medicated oral dosage form is secured within the container; and 3) a fluid propulsion device and system, such as a dishwasher, for disposing of the medicated oral dosage form, wherein the fluid propulsion device causes or directs a fluid to penetrate the container through a single aperture or the plurality of apertures in the container, thus causing the fluid to dissolve and dispose of the medicated oral dosage form.

1 Claim, 7 Drawing Sheets

U.S. PATENT DOCUMENTS

| | | | | | |
|---|---|---|---|---|---|
| 5,071,017 | A | | 12/1991 | Stull | |
| 5,111,946 | A | | 5/1992 | Glanz | |
| 5,183,156 | A | | 2/1993 | Bruno | |
| 5,223,259 | A | | 6/1993 | Lackney | |
| 5,245,117 | A | | 9/1993 | Withers et al. | |
| 5,259,501 | A | | 11/1993 | Withers et al. | |
| 5,447,247 | A | | 9/1995 | Derksen | |
| 5,511,654 | A | | 4/1996 | de la Rocha | |
| 5,593,648 | A | * | 1/1997 | Christie et al. | 134/93 |
| 5,738,234 | A | * | 4/1998 | Harrold | 206/540 |
| 6,173,851 | B1 | | 1/2001 | Hague et al. | |
| 6,253,914 | B1 | * | 7/2001 | Berg | 134/201 |
| 6,286,698 | B2 | * | 9/2001 | Hague et al. | 215/201 |
| 6,301,733 | B1 | * | 10/2001 | Dawson et al. | 134/93 |

* cited by examiner

PORTABLE CONTAINER FOR DISPOSING OF A MEDICATED ORAL DOSAGE FORM

This Application claims benefit of U.S. provisional Application Ser. No. 60/291,032 filed May 15, 2001.

BACKGROUND OF THE INVENTION

1. The Field of the Invention

This invention relates to child-resistant containers and in particular to child-resistant containers capable of disposing of medicated oral dosage forms securely contained therein.

2. Description of the Prior Art

A large number of chronically ill patients, many of whom are convalescing at home, have been prescribed opioids for the pain associated with their disease. These opioids ease most of these patients' pain, but opioid levels cannot safely be raised to account for the phenomenon of "breakthrough pain." U.S. Pat. No. 4,671,953 discloses a method for treating such breakthrough pain by administering a medicated oral dosage form, containing a strong drug such as fentanyl, in a dose-to-effect manner to such patients. Such a method has been shown to be effective in treating breakthrough pain. The method is also effective in treating post-surgical or other types of pain. A patient inserts the medicated oral dosage form into his or her mouth, and in only a few minutes, the effects of the fentanyl can be felt, relieving the breakthrough pain. Upon reaching this level of relief, some of the dosage may still be unused.

In the event that a portion does remain, there are concerns about how to properly dispose of the medicated oral dosage form. Rinsing it under water will dissolve the remaining dosage, but this technique takes time and concentration. Other patients may be tempted to discard the dosage form by throwing it in the trash. This may create potential hazards if the dosage form is discovered and used improperly by those for whom the medication is not prescribed.

Accordingly, what is needed in the art is a disposal system and container wherein a patient may store a partially consumed medicated oral dosage form in such a way as to prevent discovery and misuse of the dosage form. In addition, what is needed is a disposal system and container that allows a patient to properly dispose of the unused portion of the medicated oral dosage form, thereby preserving the security and safety provided by the container.

SUMMARY OF THE INVENTION

Two objects of the present invention are to provide an interim storage container and a disposal system for a medicated oral dosage form.

Another object of some embodiments of the present invention is to provide a container that is capable of storing a medicated oral dosage form and subsequently facilitating the disposal of such while still secured within a container.

Still another object of some embodiments of the present invention is to provide a method for disposing of medicated oral dosage forms.

A further object of some embodiments of the present invention is to provide a safe and effective way to dispose of a medicated oral dosage form.

A still further object of some embodiments of the present invention is to provide a disposal system that is capable of disposing several medicated oral dosage forms.

The present invention, in its broadest terms, includes a disposal system for disposal of medicated oral dosage forms comprising: 1) a container having a top, a bottom, and a sidewall, the container having a single aperture or a plurality of apertures located therein; 2) a means for securing a medicated oral dosage form within the container wherein the means allows the medicated oral dosage form to be easily inserted into the container, but prevents the medicated oral dosage form from being removed from the container such that the medicated oral dosage form is secured within the container; and 3) a fluid propulsion device for disposing of the medicated oral dosage form wherein the fluid propulsion device causes a fluid or liquid to penetrate the container through the apertures in the container, thus causing the fluid to dissolve and dispose of the medicated oral dosage form, the fluid easily entering and exiting the container.

The means for securing the medicated dosage form may include a device or system capable of allowing the medicated oral dosage form to pass into the container while not allowing the medicated oral dosage form to be removed therefrom the same way it was inserted. This feature performs the function of securing the medicated oral dosage form within the container where it may be stored or disposed of according to the invention as described herein. In a preferred embodiment, the means for securing is a unidirectional port having a plastic membrane with slits extending radially outward from a central point, and an opening formed in the container where access to the opening is regulated by the membrane. The unidirectional port may be included in a closure, such as a child-resistant lid. In another embodiment, the container is provided with a uni-directional port, but not a removable cap. It is important to also note that the means for securing may comprise any device or method known by those skilled in the art that allows a medicated oral dosage form to be easily placed and secured within a container.

The fluid propulsion device may also include a variety of devices and systems. However, in keeping with the technology of the present invention, the system or device must be capable of disposing of the medicated oral dosage form while it is secured within the container. In a preferred embodiment, the fluid propulsion device is a dishwasher wherein a fluid or liquid will enter the container and dissolve the partially used medicated oral dosage form. The critical characteristic that the fluid propulsion device must have is the ability to propel fluid through the apertures located at various points along the container such that the fluid contacts the medicated oral dosage form thereby dissolving and disposing of the medicated oral dosage form. As the fluid contacts the medicated oral dosage form, the sequence of continuous reactions with the water cause the medicated oral dosage form to break down and dissolve until nothing remains but the holder or stick used to carry the medicated oral dosage form. The dissolved matrix and drug are flushed from the dishwasher during its normal cycles.

In addition, it is important that the container be constructed of a material that is capable of withstanding the heat that may be associated with the dissolving operation. For example, the container should be dishwasher safe.

The apertures located on the container are placed such that fluid may enter the interior portion of the container as needed to properly dispose of the medicated oral dosage form. Their exact positioning is not critical as long as they are able to facilitate fluid entry from the exterior of the container into the interior of the container where the liquid may then dispose of the medicated dosage form. The apertures may be placed on the top or bottom of the container, or they may be placed along the sidewall of the container, or a combination of these. In any event, the apertures must be placed so that fluid, such as water, may enter the container through the apertures, dispose of the medicated oral dosage form, and then be drained from the container. It is also important to keep the apertures of a suitable dimension such that a proper amount of fluid may enter and exit the apertures while the medicated oral dosage form is being dissolved, yet small enough so that access to the medicated oral dosage form is prevented.

Finally, the present invention further features a method for disposing of a medicated oral dosage form, the method comprising the steps of: 1) inserting a medicated oral dosage form into a container, the medicated oral dosage form comprising a medicated portion and a holder; 2) placing the container in a fluid propulsion system, wherein the fluid propulsion system causes a fluid to penetrate the housing of the container to continuously contact the medicated oral dosage form, thus dissolving and disposing of the medicated potion of the medicated oral dosage form.

The method as described above may be repeated as often as necessary to dispose of any number of medicated oral dosage forms.

Additional objects and advantages of the present invention will be apparent from the following detailed description of the preferred embodiments thereof, which proceeds with reference to the accompanying drawings.

BRIEF DESCRIPTION OF THE DRAWINGS

In order that the manner in which the above-recited and other advantages and objects of the invention are obtained, a more particular description of the invention briefly described above will be rendered by reference to specific embodiments thereof which are illustrated in the appended drawings. Understanding that these drawings depict only typical embodiments of the invention and are not therefore to be considered to be limiting of its scope, the invention will be described and explained with additional specificity and detail through the use of the accompanying drawings in which.

DETAILED DESCRIPTION OF THE PREFERRED EMBODIMENTS

As stated above, the present invention, in its broadest terms, includes a disposal system for disposal of medicated oral dosage forms comprising: 1) a container having a top, a bottom, and a sidewall, the container having a plurality of apertures located thereon; 2) means for securing a medicated oral dosage form within the container wherein the means allows the medicated oral dosage form to be easily inserted into the container, but prevents the medicated oral dosage form from being removed from the container such that the medicated oral dosage form is secured within the container; and 3) a fluid propulsion device for disposing of the medicated oral dosage form wherein the fluid propulsion device directs a fluid into the container, through its apertures, thus causing the fluid to dissolve and dispose of the medicated oral dosage form, the fluid easily entering and exiting the container.

Figure 1:
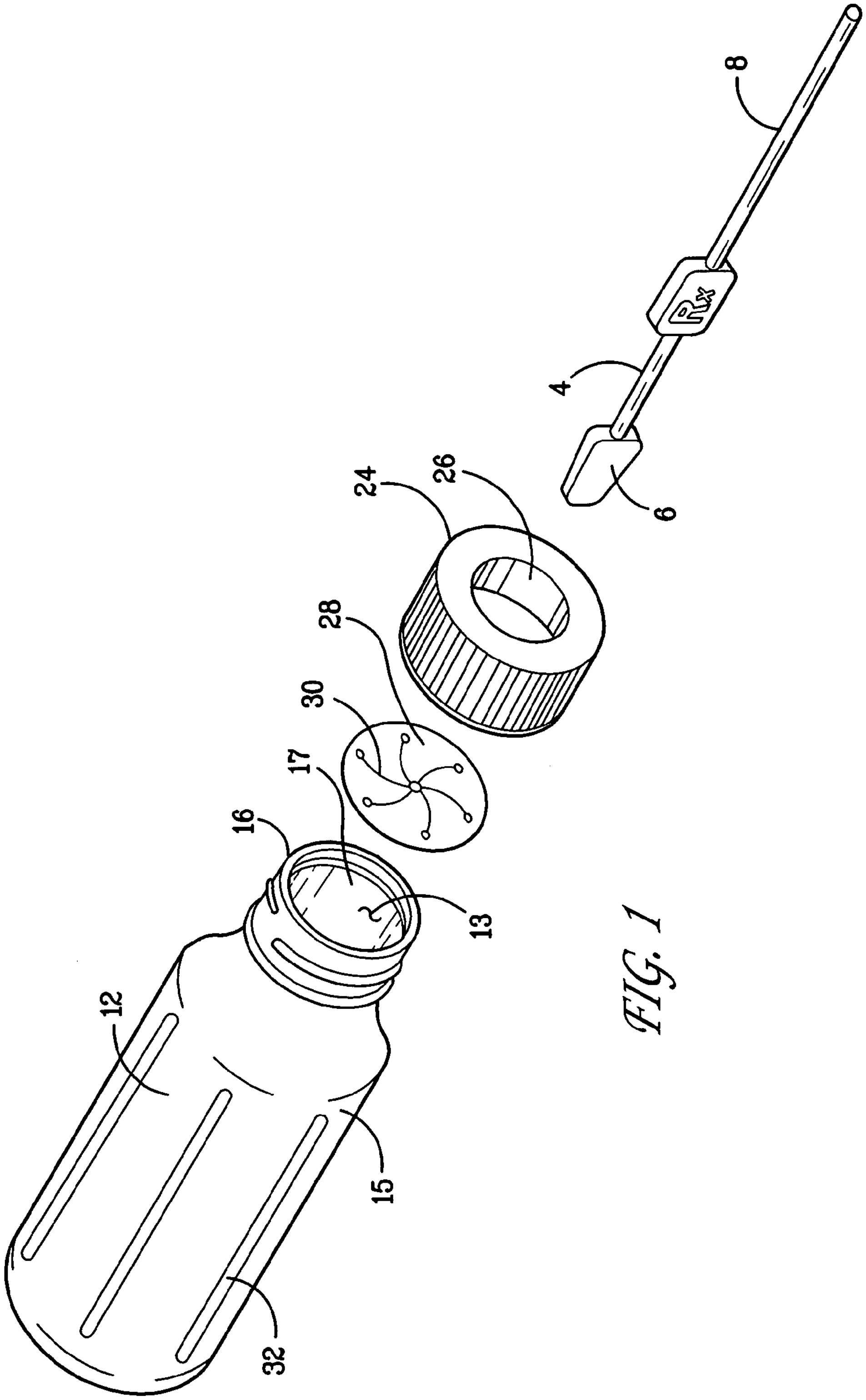
FIG. 1 illustrates a medicated oral dosage form and a disassembled container having apertures running longitudinally along the container.
Figure 2:
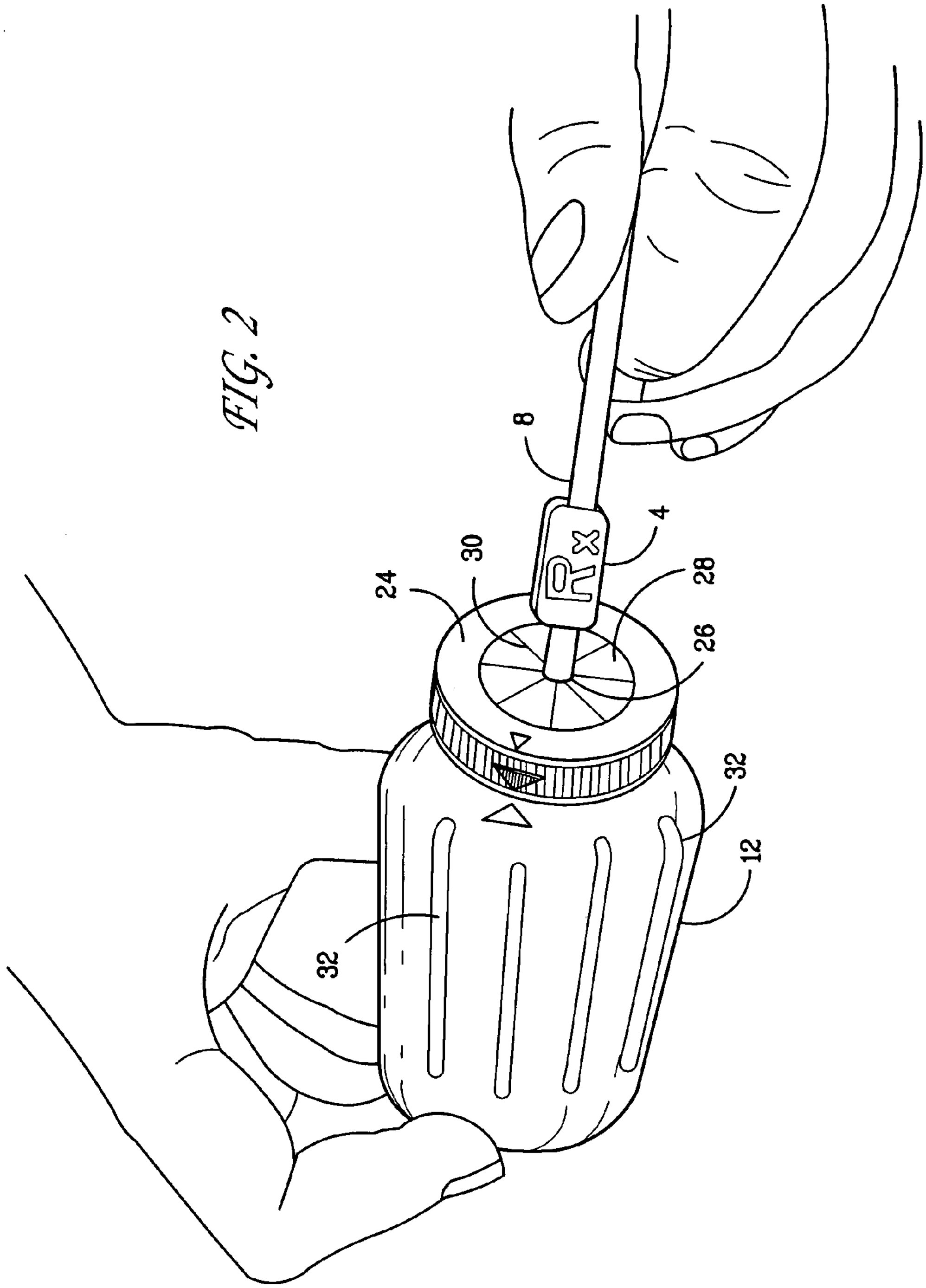
FIG. 2 illustrates the disposal apparatus and system of the present invention having a medicated oral dosage form securely contained therein.

Referring now to FIGS. 1 and 2, disposal system 10 is shown having a container 12, means for securing a medicated oral dosage form 4, wherein the means comprises a closure 24 or a lid. Closure 24 contains a uni-directional port 26 having a plastic membrane 28 with plastic membrane 28 having a series of slits 30. Unit-directional port 26 is shown within closure 24, with closure 24 shown being removably coupled to container 12. Uni-directional port may also be coupled directly to container 12 without using closure 24 or a lid. This is explained in more detail below.

Almost any of the other well-known child resistant closures are suitable for use with the present invention. Although such closures are not entirely "child resistant" in the sense that many older (and some younger) children have learned how to remove them, the term is used to refer to closures that generally prevent young children from removing such closures or that otherwise incorporate means to make a closure more difficult to remove. Similarly, the term "adult" is used in this specification to refer to anyone who can operate a "child resistant closure" without much difficulty.

In the embodiment pictured in FIGS. 1 and 2, container 12 is an opaque bottle made of high density polyethylene or other suitable material. Obviously, container 12 may be made from a transparent, or semi-transparent material. Container 12 is substantially cylindrical, having a height of approximately six inches, and a diameter of approximately one-and-a-half inches. Of course, the exact size and shape of container 12 is not important. What is critical, is that container 12 be of sufficient size so as to be able to receive a medicated oral dosage form 4 completely within its interior 13. Of course, medicated oral dosage forms like medicated oral dosage form 4 may be manufactured in various sizes and shapes. Container 12 cannot be used with a medicated oral dosage form whose size does not allow it to be completely received within interior 13 of container 12.

Formed at the top of container 12 is an opening 17 allowing relatively easy access into interior 13. Container 12 also includes a unidirectional port 26 that fits over opening 17 to allow one way access into the interior 13 of container 12. Unidirectional port 26 is approximately one-and-a-quarter inches in diameter. What is critical is that uni-directional port 26 be of sufficient size to allow medicated oral dosage form 4, which consists of a medicated portion 6 and a holder 8, to enter container 12 through opening 17. Of course, container 12 cannot be used for any medicated oral dosage forms whose size or configuration does not allow them to pass through uni-directional port 26 into container 12.

Secured to the top 16 of container 12 and extending over uni-directional port 26 is closure or lid 24. Closure 24 is a well known "child resistant" closure. As stated, closure 24 may be any suitable closure known by those skilled in the art to prevent children from gaining access to medication contained within a container or bottle.

When closure 24 is removed from container 12, access to the interior 13 of container 12 may be obtained. After medicated oral dosage form 4 has been inserted into container 12 through uni-directional port 26, medicated oral dosage form 4 can be removed from container 12 only by unlocking and removing closure 24.

From FIG. 1, it can be seen that closure 24 fits over opening 17. Opening 17 is of sufficient size that medicated oral dosage form 4 can pass through it. A plastic membrane 28, having slits 30 therein, covers opening 17. Thus, when closure 24 is placed on container 12 over opening 17, plastic membrane 28 regulates access to the interior 13 of container 12 through opening 17.

Uni-directional port 26 includes plastic membrane 28 which is a circular piece of slitted plastic fitted within closure 24 over opening 17. Plastic membrane 28 is also sized so as to fit snugly within closure 24. As an alternative, plastic membrane 28 can be mounted with adhesive or otherwise fastened over opening 17. In addition, plastic membrane 28 can be manufactured as an integral, unitary part of closure 24.

Plastic membrane 28 can take a variety of forms and configurations. FIGS. 1 and 2 show membrane 28 with slits 30 extending radially outward from a central point. The slits 30 define several segments in plastic membrane 28 and are of sufficient length to allow medicated oral dosage form 4 to pass through an opening in plastic membrane 28 that is created when medicated oral dosage form 4 is pressed against and bends plastic membrane 28. Thus, the plastic is of sufficient stiffness that some force is required to the segments, but not so much force that inserting medicated oral dosage form 4 through plastic membrane 28 and opening 17 becomes difficult. When the force is discontinued, the segments return to their original position, closing the opening in membrane 28. This secures medicated oral dosage form 4 within interior 13 of container 12 as medicated oral dosage form is prohibited from passing back through uni-directional port 26 due to its design. Because medicated oral dosage form 12 cannot pass back through plastic membrane 28 without the application of force, and because the only potential force available to press medicated oral dosage form 4 against plastic membrane 28 within container 12 is its own weight, slitted membrane 28 substantially prevents medicated oral dosage form 4 from passing out of container 12. Any number of other slit patterns may be used.

Also shown in FIGS. 1 and 2 are a plurality of apertures 32. Apertures 32 are shown running longitudinally along container 12. Apertures 32 are dimensioned and placed along container 12 so that as container 12 is subjected to a fluid propulsion device, such as a dishwasher, the propelled fluid will penetrate container 12 through apertures 32 and contact medicated oral dosage form 4 contained therein. Apertures 32 also allow any fluid to exit interior 13 of container 12 to allow a continuous flow of fluid through container 12 enabling medicated oral dosage form 4 to be disposed of more efficiently. The fluid contact will ultimately dissolve and dispose of medicated oral dosage form 4. Apertures 32 may be positioned depending upon the type of fluid propulsion device used. As different devices may be used, so too may the size, number, and placement of apertures 32 be varied to accommodate the different devices.

Apertures 32 are large enough to allow a fluid to pass from the exterior 15 of container 12 to the interior 13 of container 12 where medicated oral dosage form 4 is securely contained. However, apertures 32 must not be too large so as to permit improper access or unauthorized access to medicated oral dosage form 4. As container 12 is preferably opaque, this will help in concealing medicated oral dosage form 4. FIG. 2 shows the disposal system 10 having medicated oral dosage form 4 secured therein.

Figure 3:
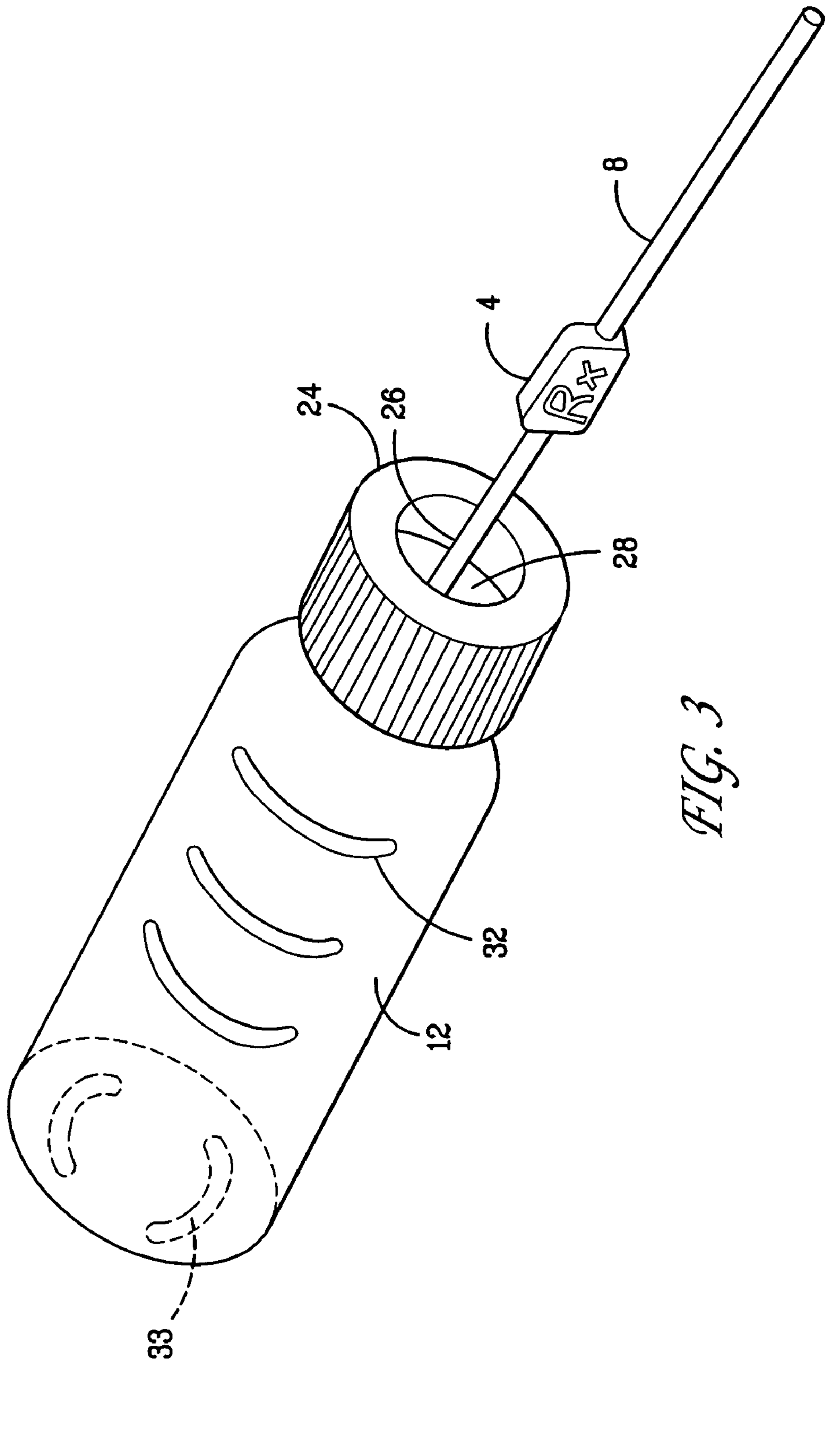
FIG. 3 illustrates the disposal apparatus and system having apertures running transversely along the circumference of the container.

FIG. 3 depicts another embodiment of the present invention where apertures 32 are spaced transversely along container 12. Also shown is container 32 having apertures, or drains 33 along its bottom surface 18. These apertures located along bottom surface 18 allow any fluid that was used to dispose of medicated oral dosage form 4, and any solution of fluid and medication from the disposal of medicated oral dosage form 4, to drain from interior 13 of container 12. Apertures 32 running transverse along container 12 are shown being spaced apart from each other and not extending entirely around container 12. The particular size and length of apertures 32 is not critical. They must however, be of a suitable dimension to allow a fluid to enter and exit the interior 13 of container 12 to properly dispose of medicated oral dosage form 4. FIG. 3 also shows that an aperture 33 located in the bottom surface of container 12 may be used in conjunction with opening 17 if no other apertures are present on container 12 and the fluid propulsion device is capable of directing fluid through opening 17 enough to properly dissolve and dispose of the medicated oral dosage form.

Figure 4:
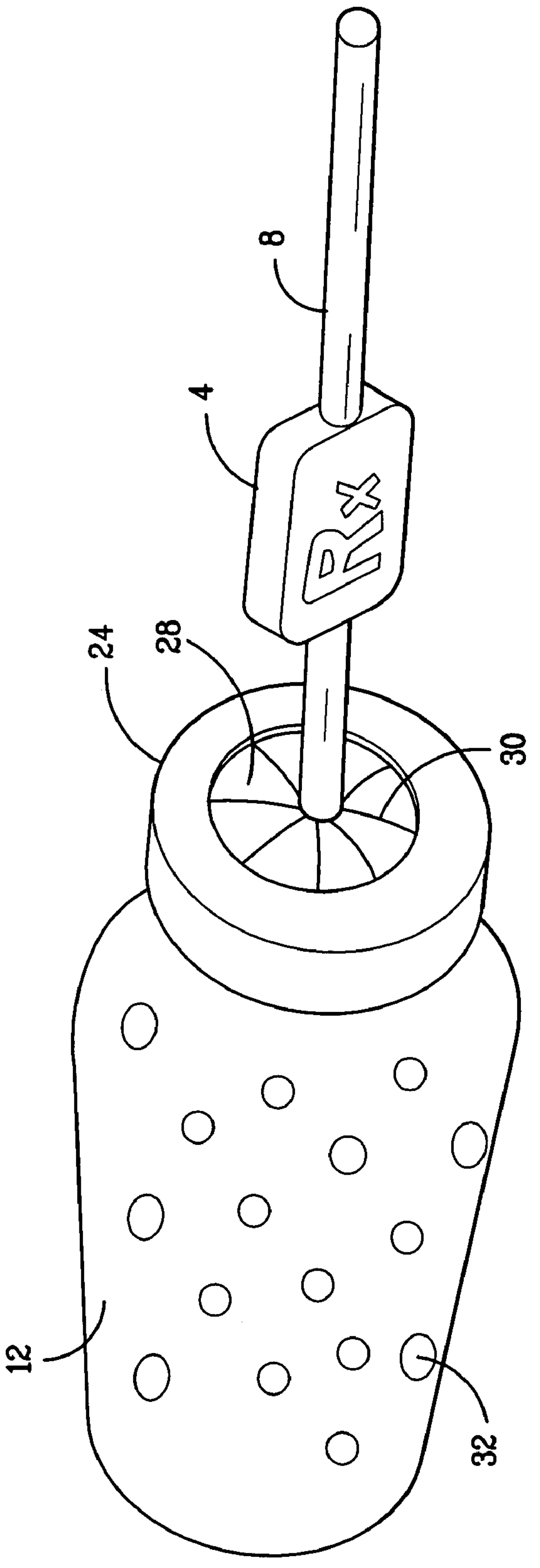
FIG. 4 illustrates the disposal apparatus and system having a series of individual apertures randomly spaced along the container.

FIG. 4 shows yet another embodiment of the present invention wherein apertures 32 are individual intermittently spaced holes all around container 12. These holes must also be of a suitable dimension so as to allow fluid to pass through the holes and into the interior 13 of container 12, yet small enough to prohibit unauthorized access to medicated oral dosage form 4 securely contained therein.

Figure 5:
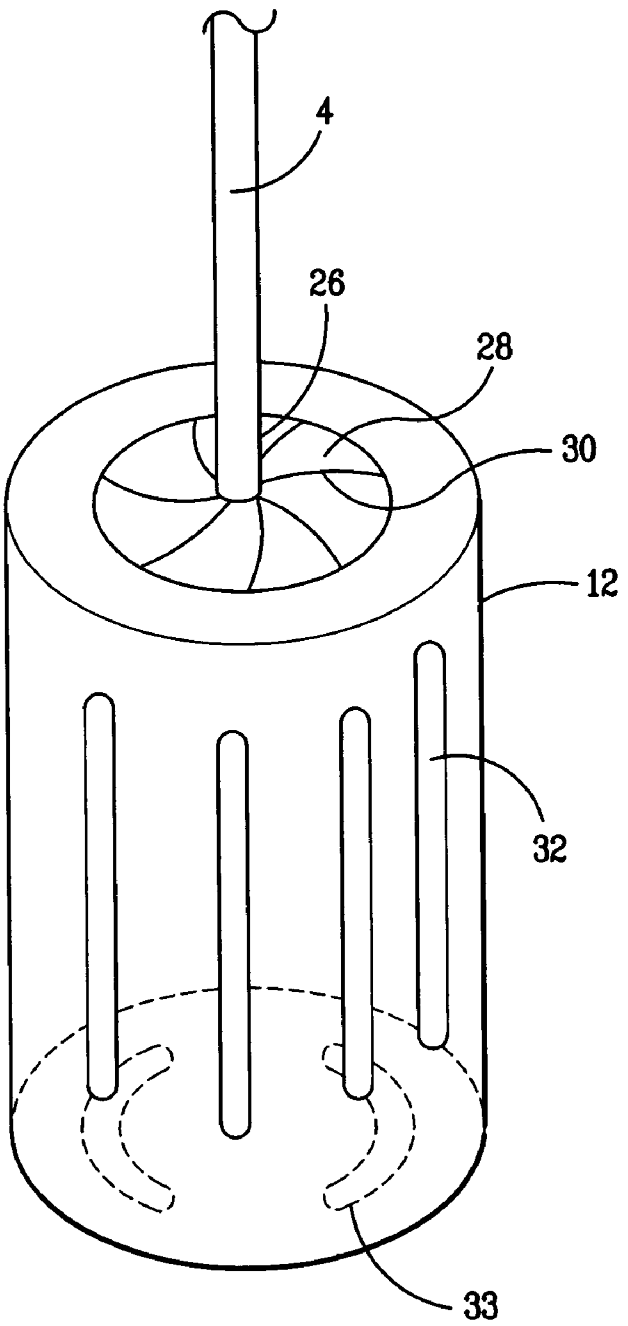
FIG. 5 illustrates the disposal apparatus and system having a different shape and without a top portion or lid, the means for securing a medicated oral dosage form built into the housing of the container.

FIG. 5, shows an embodiment of the present invention consisting of container 12 having no top or closure portion coupled thereto. Unlike the previous embodiments where the means for securing a medicated oral dosage form within container 12 consisted of a uni-directional port contained within a child-resistant lid, the embodiment shown in FIG. 5 includes a container 12 having a built-in means for securing a medicated oral dosage form within container 12. Uni-directional port 26 is still shown as the preferred means for securing medicated oral dosage form 4 within container 12. However, because of the purpose and objects of the present invention to dispose of medicated oral dosage form as it is securely contained within container 12, no lid is required. Once the medication has been properly used and the user desires to dispose of the medication, all that is needed is to insert the medicated oral dosage form 4 through uni-directional port 26 so that is securely contained within container 12. Due to the presence of apertures 32, container 12 may then be subjected to a fluid propulsion device where the fluid will penetrate container 12 through apertures 32 and dissolve and dispose of medicated oral dosage form 4. In addition to using a fluid propulsion device, the medicated oral dosage form may also be dissolved by pouring water, preferably warm soapy water, through the means for securing. Container 12 may then be shaken to dissolve the medicated oral dosage form. When the dosage form is dissolved, the container can be inverted to drain the solution. Although the holder or handle will remain inside this embodiment, the container has enough extra space to be used several times before the handles will impede the introduction of additional partially consumed medicated oral dosage forms.

As mentioned, disposal system 10 and container 12 placed can be placed within a dishwasher, or other suitable fluid propulsion device. When the patient determines that the medication cycle is complete, or wishes to dispose of the medicated oral dosage form early, the dosage form may be placed within a dishwasher where the water pressure and heat contained therein will penetrate container 12 and contact medicated oral dosage form 4. As the dishwasher cycle progresses, water will enter and exit container 12 through apertures 32, thus dissolving and disposing of medicated oral dosage form 4. Any excess water or solution may be dumped out through apertures 32, or drained therefrom by an aperture located in the bottom 18 of container 12.

Figure 6:
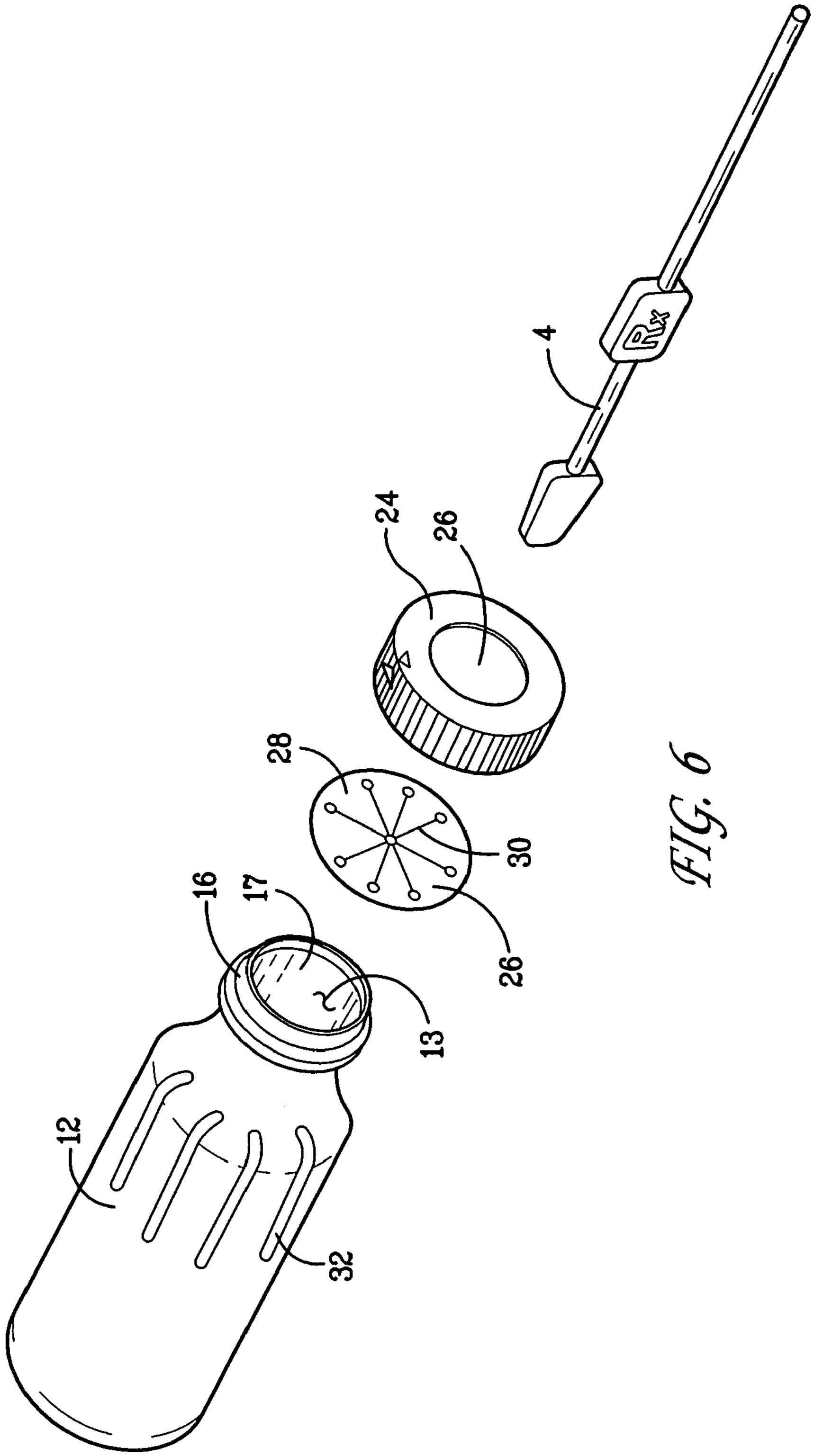
FIG. 6 illustrates the disposal apparatus and system having no apertures, but a main unidirectional port and associated aperture.

FIG. 6 illustrates another alternative embodiment, wherein the disposal system 10 and container 12 has apertures 32 in only the upper half of container 12. In this embodiment container 12 is again equipped with uni-directional port 26 to secure medicated oral dosage form 4 therein. Here, a user is able to pour a dissolving liquid or agent into the interior of container 12, wherein medicated oral dosage form 4 is either dissolved over time, or container 12 may be shaken such that the resulting agitation of the liquid dissolves medicated dosage form 4 therein. Upon dissolution of medicated oral dosage form 4, the resulting mixture can then be disposed of properly by pouring out the liquid from port 26 and apertures 32. In essence, this embodiment would allow container 12 to act as a fluid flow through system (e.g. if put in the dishwasher), or a flow through, soak, and flush system (e.g. allowing fluid to penetrate the container, then sit in the container where the medicated form is dissolved, and then the fluid mixture flushed or removed from the container). This embodiment may utilize closure or lid 24 along with uni-directional port 24, or may have uni-directional port 26 built-in to container 12.

Although not shown in the drawings, an obvious variation to each of the embodiments described herein would be a container having no apertures in the housing except for the single aperture used to allow a medicated oral dosage form to be inserted into the interior of the container. This would allow the container to be completely filled with a liquid/fluid for dissolving the dosage form contained therein. Once the dosage form was dissolved, the fluid mixture could then be disposed of by dumping the mixture out through the single aperture.

Figure 7:
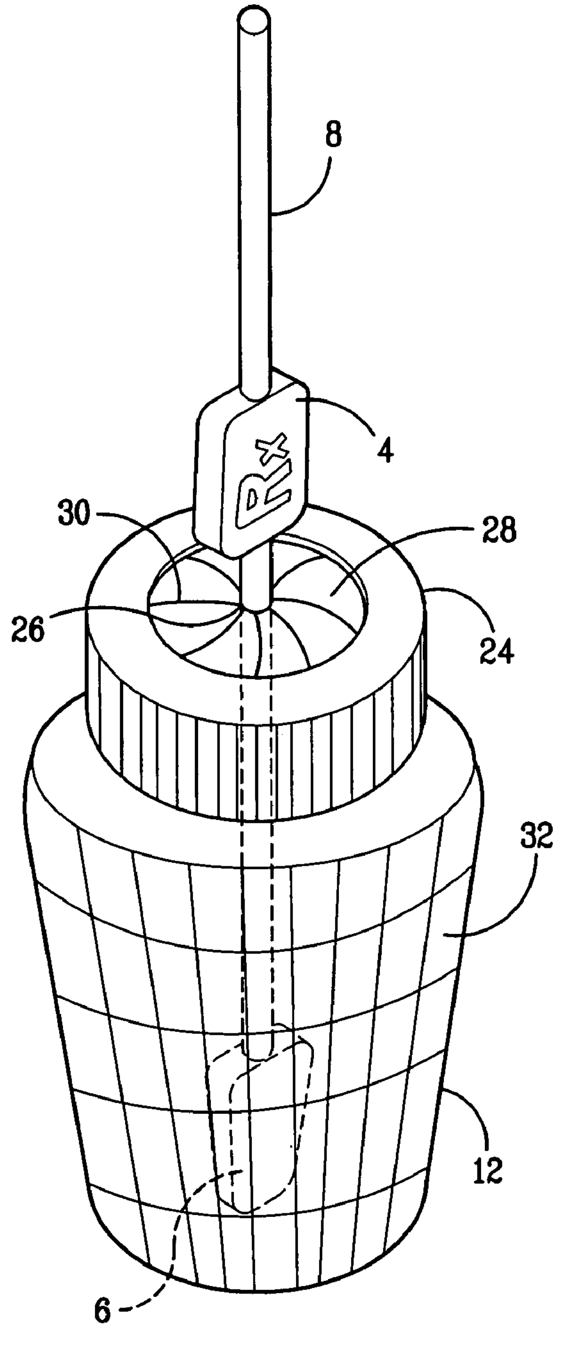
FIG. 7 illustrates an alternative embodiment of the disposal apparatus and system, wherein the container comprises a framework, such as a metal or plastic wire-frame.

FIG. 7 illustrates yet another embodiment of the present invention, wherein container 12 comprises a framework, such as a wireframe or cage or basket structure as shown. The framework includes a plurality of apertures 32 wherein fluid may pass to dissolve a medicated dosage form 4 secured therein. The framework container may be equipped with a child proof or child resistant lid 24 such as described above, with or without a uni-directional port 26, or the framework container may contain the uni-directional port as a built-in feature of the container. In addition, the framework may be made of metal or plastic. The framework container is capable of being placed in a dishwasher or other fluid propulsion system wherein medicated oral dosage form 4 contained therein may be disposed of. The framework container may also be subject to other forms or methods of disposing medicated oral dosage form 4, such as placing container 12 in a liquid bath wherein the form 4 may dissolve over time.

The present invention further features a method for disposing of a medicated oral dosage form. The method comprises the steps of: 1) inserting a medicated oral dosage form into a container; 2) placing the container in a fluid propulsion system, wherein the fluid propulsion system causes fluid to penetrate the housing through said apertures to continuously contact the medicated oral dosage form, thus dissolving and disposing of the medicated oral dosage form; and 3) removing said holder from said container once said medicated portion is dissolved and disposed of.

This method may be repeated any number of times and for any number of medicated oral dosage forms.

Based on the foregoing, the present invention may be embodied in other specific forms without departing from its spirit or essential characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

The invention claimed is:

1. A portable container for storing and disposing of medicated oral dosage forms, said container comprising:

a housing having an interior and an exterior and comprising a metal framework structure wherein said framework structure consists of a cage structure;

a child-resistant lid having a uni-directional port operable with said housing, said port allowing a medicated oral dosage form to pass uni-directionally through said port and into said interior of said housing, said uni-directional port securing the medicated oral dosage form within said housing of said container; and a plurality of apertures formed in said housing, said plurality of apertures allowing a fluid to enter into said housing by placing said housing in a liquid bath or a dishwasher, to dissolve the medicated oral dosage form, wherein said plurality of apertures allows for infinite dilution of the medicated oral dosage form.

* * * * *